United States Patent [19]

Dechene et al.

[11] 4,291,273

[45] Sep. 22, 1981

[54] FLOW REGIME DETECTING

[75] Inventors: Ronald L. Dechene, Boxford; Frank G. Grimaldi; Robert E. Newton, both of Tewksbury, all of Mass.

[73] Assignee: Auburn International, Inc., Danvers, Mass.

[21] Appl. No.: 48,765

[22] Filed: Jun. 14, 1979

[51] Int. Cl.³ .......................................... G01N 27/42
[52] U.S. Cl. ................................................... 324/343
[58] Field of Search ........................................ 324/434

[56] References Cited

U.S. PATENT DOCUMENTS 4,063,153  12/1977  Dechene ............................. 324/434

Primary Examiner—Michael J. Tokar
Attorney, Agent, or Firm—Jerry Cohen

[57] ABSTRACT

Measuring of mixed phased flows to determine flow regime through the use of circumferentially shifted electric fields and measurement of resultant diametral and chord conductances with certain combinations of ratios of diametral to cord conductances serving as a signature of flow regime.

4 Claims, 6 Drawing Figures

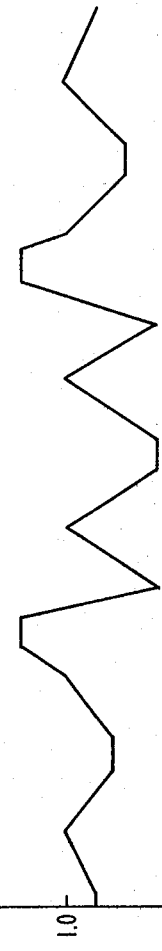
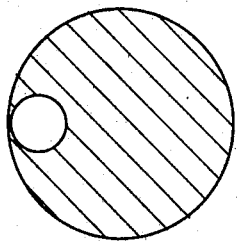
FIG. 6B
FIG. 6A
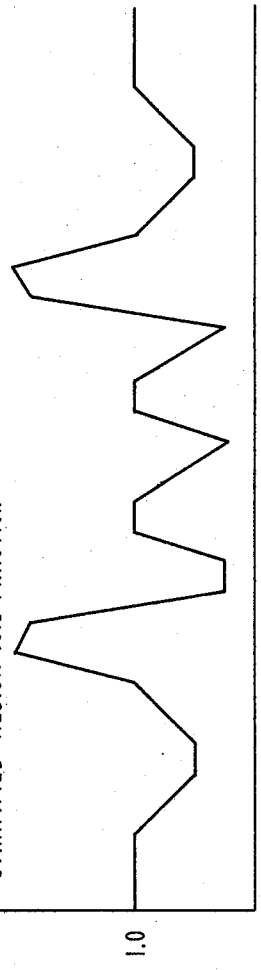
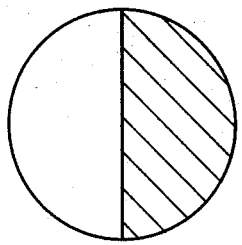
FIG. 7B
FIG. 7A
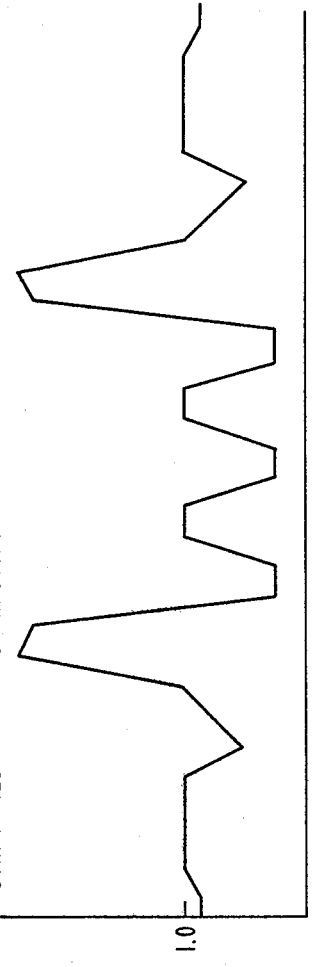
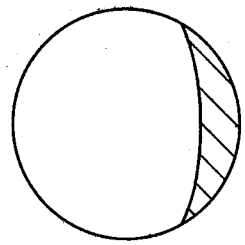
FIG. 8B
FIG. 8A

FLOW REGIME DETECTING

BACKGROUND OF THE INVENTION

The present invention relates to determination of flow regime, an important consideration in a variety of mixed phase flows, including boiling water conduits and many other applications. The state of the art of flow regime determination for boiling water conduits, particularly associated with power plants is set forth in the final report (NP 118) prepared by Heat Transfer and Fluid Flow Service of the Atomic Energy Research Establishment of Harwell, England, for the Electric Power Research Institute, 3412 Hillview Avenue, Palo Alto, Cal. 94304, U.S.A., dated March 1976 entitled "Experimental Methods in Two-Phase Flow Studies." That paper reports the state of the art as comprising, for purposes of flow regime determination, visual and photographic methods, contact methods, electrochemical measurements in re shear stresses, X-ray fluctuations, pressure fluctuation analysis and multi-beam X-ray methods. None of these methods have achieved widespread acceptance nor have shown themselves to be wholly adequate in terms of all the relevant criteria.

It is an important object of the present invention to provide a new method of flow regime detection combining reliability of measurement with high measurement speed, usability under various void fraction concentration conditions, adaptability to a variety of fluids, nondisturbance of the flow condition to be determined, all consistent with low bulk, weight and cost of associated equipment.

SUMMARY OF THE INVENTION

In accordance with the invention an electrical conductance measuring technique is used starting with equipment substantially as described in U.S. Pat. No. 4,063,153 granted Dec. 13, 1977, of common assignment with the present application. Early tests with the patented apparatus showed some flow regime sensitivity, which was defeated by inability to simultaneously correlate basic flow regime with void fraction, i.e. a flow regime A and void fraction concentration B might resemble a flow regime C with a void fraction concentration D.

The patented apparatus was modified to overcome such problems and for purposes of flow regime now comprises, an array of electrodes around the cross-section plane of a flow conduit, substantially as described in the patent, an oscillator for sequentially exciting the electrodes, creating circumferential sequences of one transmit electrode oppositely poled with a receiver electrode creating at any given moment an electrical field which is asymmetrically arranged with respect to the flow conduit. Conductance can be measured between diametrally opposed electrodes and between electrodes opposed along a chord of the conduit, (i.e. the latter field being between alternate electrodes or two adjacent electrodes). Diametral conductance should be significantly lower than chord conductance under properly selected conditions and with the same conductive fluid filling all the conduction paths. The ratio of such conductances is measured. Where the ratio of diametral conductance to chord conductance is greater than 1.0, this is correlatable with the absence of some of the conductive fluid between the activated electrodes constituting the chord path. Sweeping such a field circumferentially around a conduit and taking similar diametral conductance to chord conductance ratios can provide a picture of separated flow along substantial portions of a conduit wall. Conversely, ratios of diametral to chord conductance substantially below that normally encountered with a zero void conductive fluid flow indicate that there may be a central void in the flow.

The mixed phase fluid typically comprises gas voids in a conductive liquid, but may comprise non-conductive solids as the "void" material. The techniques of the invention may also be applied to immiscible multiple liquid flows where there is a significant difference between conductances of the two immiscible liquids.

Other objects, features and advantages of the invention will be apparent from the following detailed description of preferred embodiments thereof taken in connection with the accompanying drawing in which,

DETAILED DESCRIPTION OF PREFERRED EMBODIMENTS

Figure 2:
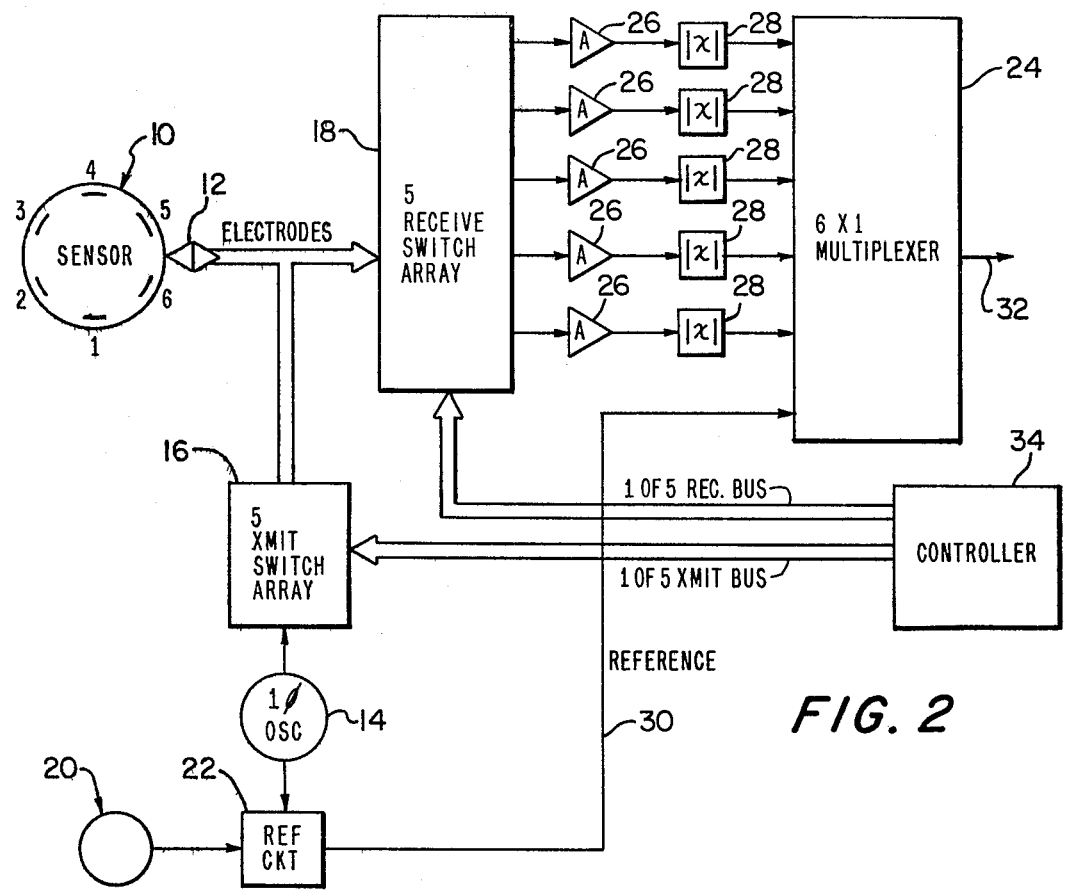
FIG. 2 is a block diagram of the system of a preferred embodiment of the invention.
Figure 1:
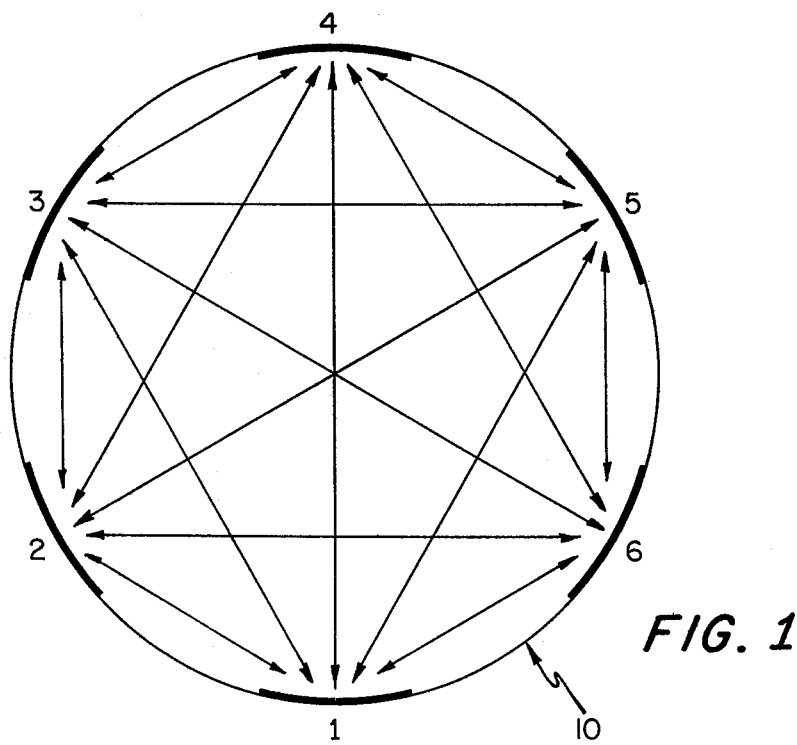
FIG. 1 is a cross section of a conduit in which flow regime is evaluated in accordance with a preferred embodiment of the invention.

FIG. 1 shows a conduit 10 with electrodes 1, 2, 3, 4, 5, 6 therein spread in annular array therearound, and FIG. 2 shows the electrode control circuit utilized for flow regime evaluation in accordance with a preferred embodiment of the invention. While shown inside the conduit for illustration, it will be appreciated that in practice the electrodes will be integrated into the wall of the conduit as shown for instance in the patent cited above. Interconnections to the electrodes are schematically indicated at 12 and they are connectable to a single phase oscillator 14 (5-10 kilohertz) via a 5 transmit switch array 16 known per se. The electrodes are also connectable to a 5 receive switch array 18 also known per se to sequentially place one electrode at a time in the position of a transmit electrode (1-5) and 1 electrode at a time (2-6) (via the 5 switch array) in the position of a receive electrode, connectable to a multiplexer 24 via amplifiers 26 and absolute value circuits. A reference conduit 20, located close to conduit portion 10 is also provided and with a reference circuit 22 also excitable by oscillator 14 to provide a voltage to a pair of electrodes (not shown) in conduit 20 and apply a current (conductance signal) to the multiplexer 24. A signal 32 is developed which is varying with time and can be mesured to show the current through the reference circuit and 5 receive electrodes within the conduit 10, all within a switch cycle step before changing the electrodes which are to be transmit and receiver electrodes. The signal 32 can be applied to an analog to digital converter and data processed, and displayed on a cathode ray tube or strip chart recorder or the like.

The usage of the reference signal compensates for changes in bulk conductivity for consistency of result.

Figure 3B:
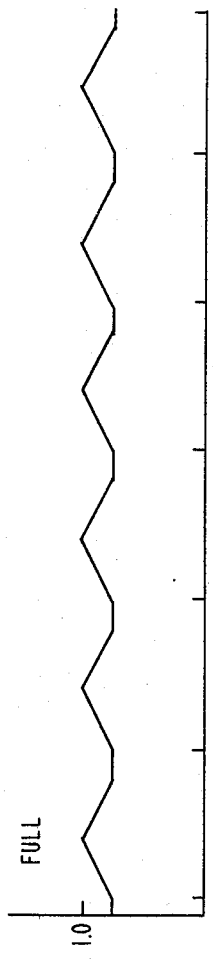
FIGS. 3A-3B, 4A-4B, et seq. are in each such A-B combination of a core cross section sketch of a particular flow regime (A) and a corresponding graphical trace (B) of diametral to chord conductance ratio versus time taken over 5 switching steps of circumferential sequencing of the electrical field to get a complete profile for one 360° scan.
Figure 3A:
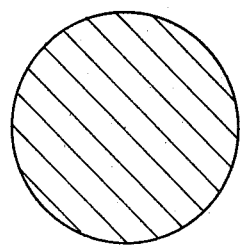

FIG. 3A shows in cross section a condition of 100% (or nearly so) liquid flow in conduit 10 with no voids. Under such conditions the ratio of diametral to chord conductance displayed in FIG. 3B is substantially 1 at each step of making one of the electrodes 1-5 a transmit electrode and one of the other electrodes 2-6 a receive electrode.

Figure 4B:
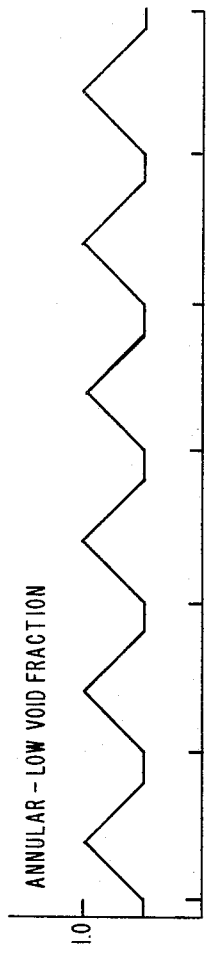
Figure 4A:
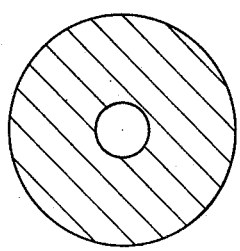

FIG. 4A shows a void formed at the center of the flow and FIG. 4B shows the resultant change in traces over the various switching steps, quite different from FIG. 3B and distinguishable therefrom.

Figure 5B:
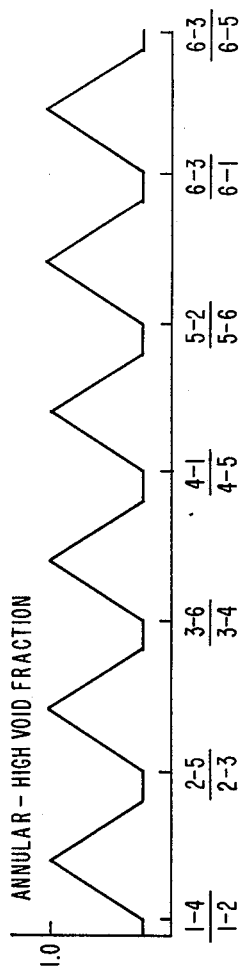
Figure 5A:
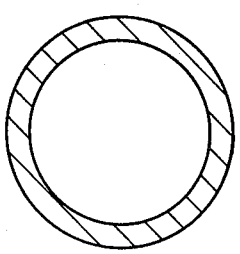

In FIG. 5A a much larger gas center is shown compared to FIG. 4A and resultant trace of FIG. 5B is quite different from FIG. 4B.

FIGS. 6A-6B show the appearance and the graphical representation of bubble/stratified flow with a low void fraction. FIGS. 7A and 7B show the effect of stratified flow with a medium void fraction and FIGS. 8A and 8B show stratified flow with a high void fraction.

It is evident that those skilled in the art, once given the benefit of the foregoing disclosure, may now make numerous other uses and modifications of, and departures from the specific embodiments described herein without departing from the inventive concepts. Consequently, the invention is to be construed as embracing each and every novel feature and novel combination of features present in, or possessed by, the apparatus and techniques herein disclosed and limited solely by the scope and spirit of the appended claims.

What is claimed is:

1. Method of determining phase cross-section distribution of mixed phase fluids comprising, establishing a cyclically rotating pattern of substantially limited, to less than full cross section, diametral and chord voltage fields and measuring the diametral and chord conductances under said voltage fields, establishing ratios of essentially simultaneous diametral and chord conductances, providing a signal based on said ratios.

2. Apparatus for determining phase cross-section distribution of mixed phase fluids comprising, a conduit, electrodes arranged in a cross-section of said conduit in a peripheral array, means for rotatably establishing different arrays of oppositely poled electrodes, means for measuring diametral and chord conductances, taking the ratio thereof in different combinations and providing a useful signal therefrom.

3. Apparatus in accordance with claim 2 wherein six equally sized, peripherally equally spaced electrodes are provided as Nos. 1 to 6 and excited in a 1 to 5 sequence with No. 1 excited in one poled sense and Nos. 2, 3, 4, 5 or 6 excited in the opposite sense, then $\frac{2}{3}$, 4, 5, or 6, then $\frac{3}{4}$, 5, or 6, then 4/5, or 6, then 5/6, then repeating cyclically, the measured conductance ratios being based on conductances obtained under the said diametral fields to conductances obtained between opposite electrodes, $\frac{1}{4}$, 2/5, 3/6, 4/1, 5/2, 6/3, respectively.

4. Apparatus in accordance with claims 2 or 3, and further comprising means for compensating for bulk conductivity changes of fluid going through the conduit.

* * * * *